(12) United States Patent
Messerly (10) Patent No.: US 8,083,739 B2
(45) Date of Patent: Dec. 27, 2011

(54) TWO-PIECE JAW FOR BIPOLAR ABLATION DEVICE

(75) Inventor: Jeffrey D. Messerly, Cincinnati, OH (US)

(73) Assignee: AtriCure, Inc., West Chester, OH (US)

( * ) Notice: Subject to any disclaimer, the term of this patent is extended or adjusted under 35 U.S.C. 154(b) by 923 days.

(21) Appl. No.: 12/104,568

(22) Filed: Apr. 17, 2008

(65) Prior Publication Data

US 2008/0275446 A1    Nov. 6, 2008

Related U.S. Application Data

(60) Provisional application No. 60/915,534, filed on May 2, 2007.

(51) Int. Cl.
*A61B 18/14* (2006.01)

(52) U.S. Cl. ............... 606/51; 606/41; 606/52; 606/205
(58) Field of Classification Search ............. 606/50–52, 606/205–207
See application file for complete search history.

*Primary Examiner* — Linda Dvorak
*Assistant Examiner* — Amanda Scott
(74) *Attorney, Agent, or Firm* — Cook Alex Ltd.

(57) ABSTRACT

A method and device for transmural ablation using an electrosurgical device having a pair of angled clamping jaws designed to be disassembled outside the patient and reassembled within the patient in a series of method steps. This disassemble and reassemble design of the electrosurgical device fits within the narrow gap between ribs of the patient, and offers unusual opportunities to work in difficult to access areas such as the thoracic cavity. Once the surgery has been performed, the electrosurgical device can be disassembled in the patient and removed one piece at a time, or removed as a unit.

20 Claims, 8 Drawing Sheets

TWO-PIECE JAW FOR BIPOLAR ABLATION DEVICE

CROSS-REFERENCE TO RELATED APPLICATION

This application claims the benefit of the filing date of U.S. Provisional Application Ser. No. 60/915,534, filed May 2, 2007, the entire contents of which is incorporated herein by reference.

BACKGROUND OF THE INVENTION

The present disclosure relates to surgical instruments, with examples relating to cardiovascular pacing devices, systems for controlling such devices, and methods for using such devices. Surgery generally refers to the diagnosis or treatment of injury, deformity, disease, or other conditions. More specifically, the present disclosure relates to electrosurgical devices with electrode assemblies that can be disassembled outside of a patient and reassembled within a patient.

A significant need exists for an electrosurgical device and a method of use that can gain access to internal tissue in difficult to access areas through a small incision. Such a surgical device could be used in the thoracic cavity and inserted intercoastally between the ribs through a small incision. The surgical device can have electrode sections that can be disassembled outside of the patient, inserted into the patient as one or more sections, and reassembled within the patient to create a clamp and coagulation device. Additionally, the surgical device can be disassembled in the body and then removed as one or more separate electrode sections.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present disclosure.

DETAILED DESCRIPTION

The following description of certain examples of an ablation device should not be used to limit the scope of the present application. Other examples, features, aspects, embodiments, and advantages of the device will become apparent to those skilled in the art from the following description, which is by way of illustration, one of the best modes contemplated. As will be realized, the device is capable of other different and obvious aspects. Accordingly, the drawings and descriptions should be regarded as illustrative in nature and not restrictive.

Figure 1:
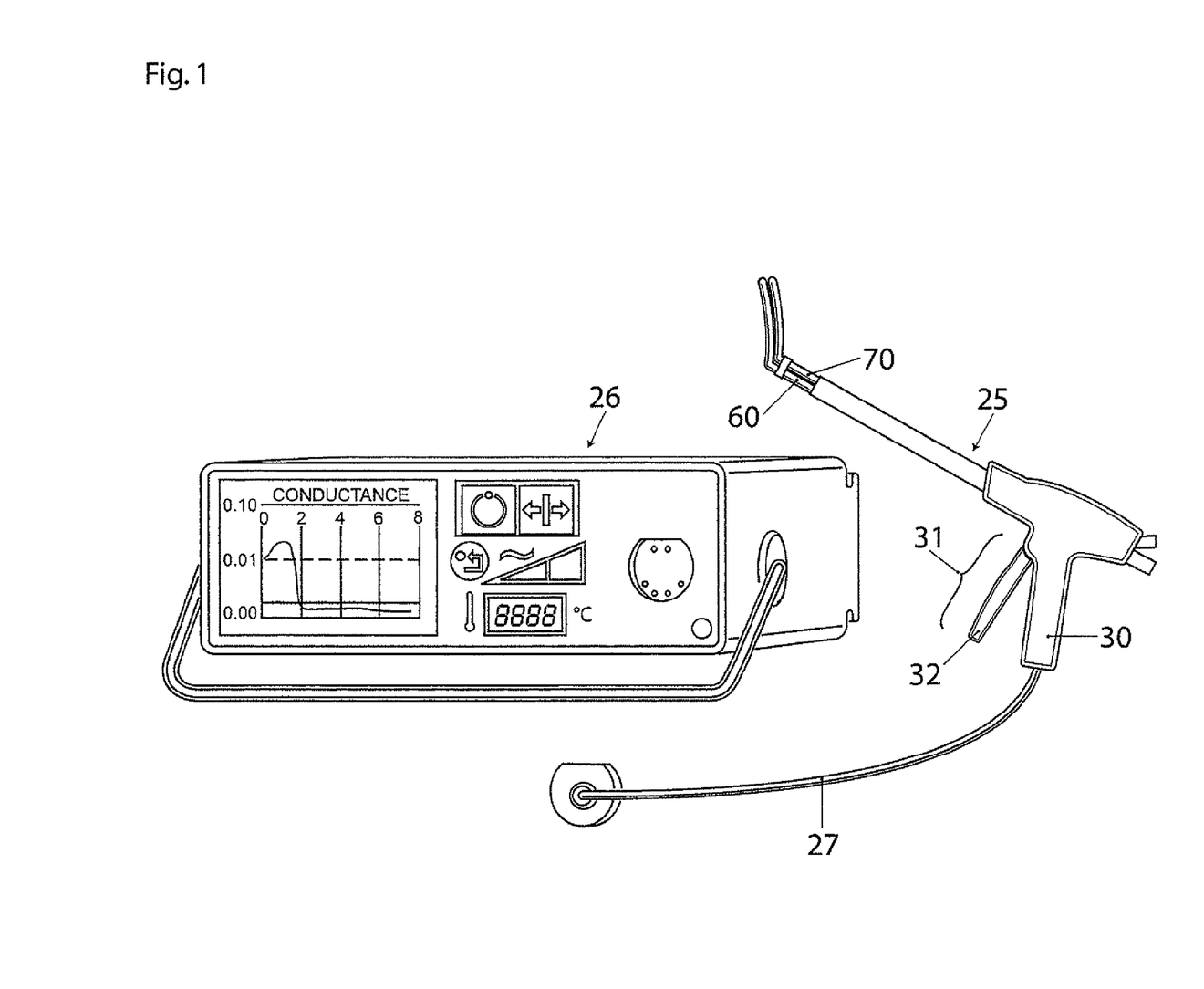
FIG. 1 is an isometric view of a two piece jaw bipolar ablation device and a electrosurgical generator.

FIG. 1 shows a two piece jaw bipolar electrosurgical device 25 attachable to a generator 26 with a cable 27. The electrosurgical device 25 has a pair of angled clamping jaw assemblies designed to be disassembled outside the patient and reassembled within the patient. Each jaw assembly has a different pole electrode in the angled clamping jaws. This disassemble and reassemble design fits within the narrow gap between ribs of the patient, and offers unusual opportunities to position the device and work on tissue that is difficult to access such as heart or vascular tissue within the tight thoracic cavity. Once the surgery has been performed, the electrosurgical device 25 can be disassembled in the patient and removed one piece at a time, or removed as a unit.

Figure 3:
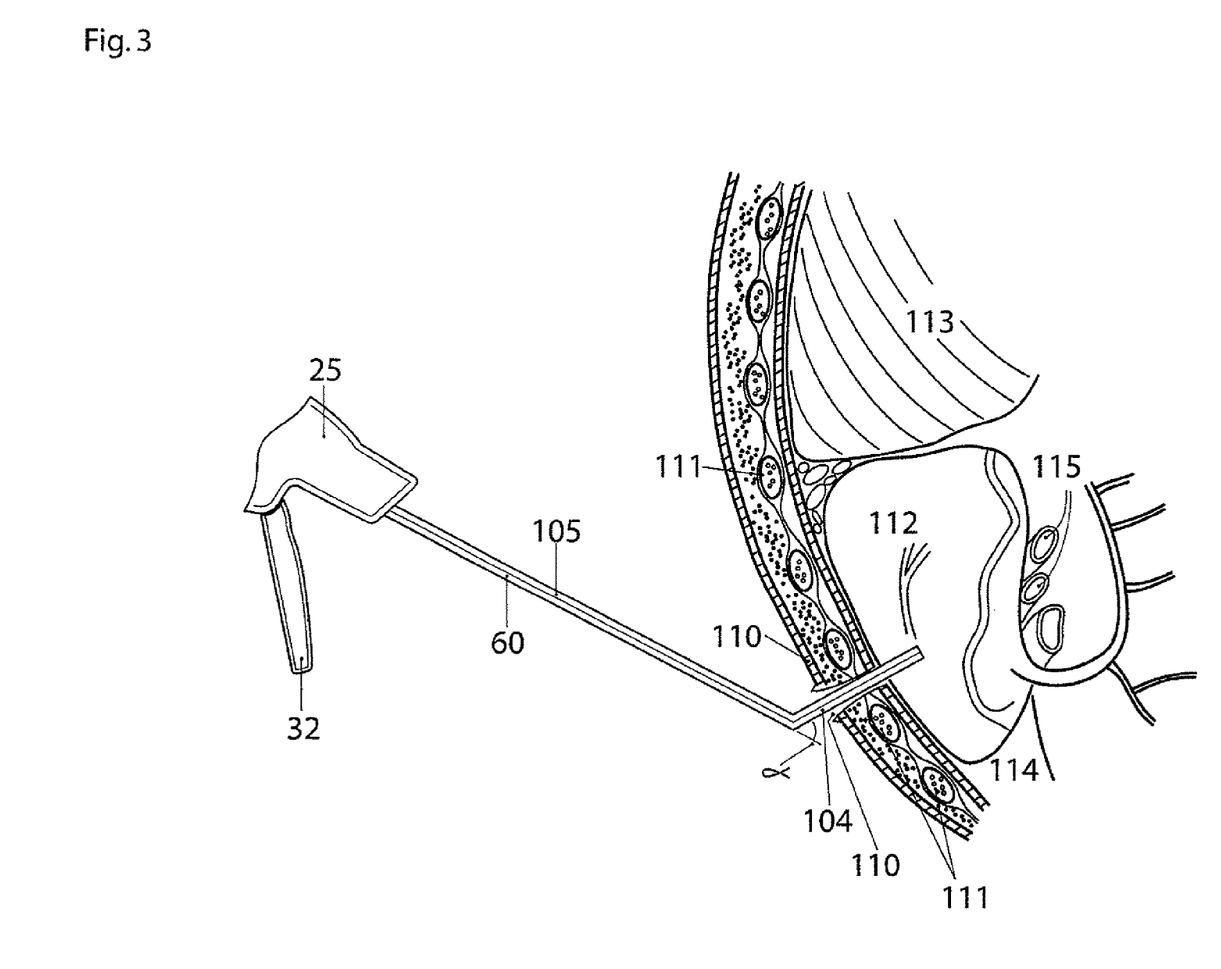
FIG. 3 is a partial cross sectional view of a patients chest and heart with a first jaw of the two piece jaw bipolar ablation device being inserted between the ribs.

In FIG. 1, a first jaw assembly 60 is fixedly attached to the handle assembly 30, and a second jaw assembly 70 is shown removably attached to the handle assembly 30. The first jaw assembly includes a first portion 104 which carries the electrode (described below) and is disposed at an angle α with respect to the longitudinal axis of the jaw assembly, as best seen in FIG. 3. The angle may vary, but is preferably about 30 degrees. The second jaw assembly 70, when attached to the handle assembly 30, operably connects to a closure trigger assembly 31 in handle assembly 30 and moves towards and away from first jaw 60 in response to movement of closure trigger assembly 31. Connection of second jaw assembly 70 to handle assembly 30 also electrically connects second jaw assembly 70 to cable 27 for the application of RF energy to tissue. In FIG. 1, the closure trigger assembly 31 is actuated to a closed position to move the second jaw assembly 70 to a closed position near the fixed first jaw assembly 60. Both first jaw assembly 60 and second jaw assembly 70 include a first pole electrode 100 and a second pole electrode 101 at an angle to the electrosurgical device 25. Each of the first pole and the second pole electrodes (100, 101) are electrically isolated in a first electrical isolator 102 and a second electrical isolator 103 respectively. The electrodes 100, 101 and electrode isolators 102, 103 are mounted within the angled jaw portions to clamp and apply RF energy to tissue clamped therebetween.

Figure 2:
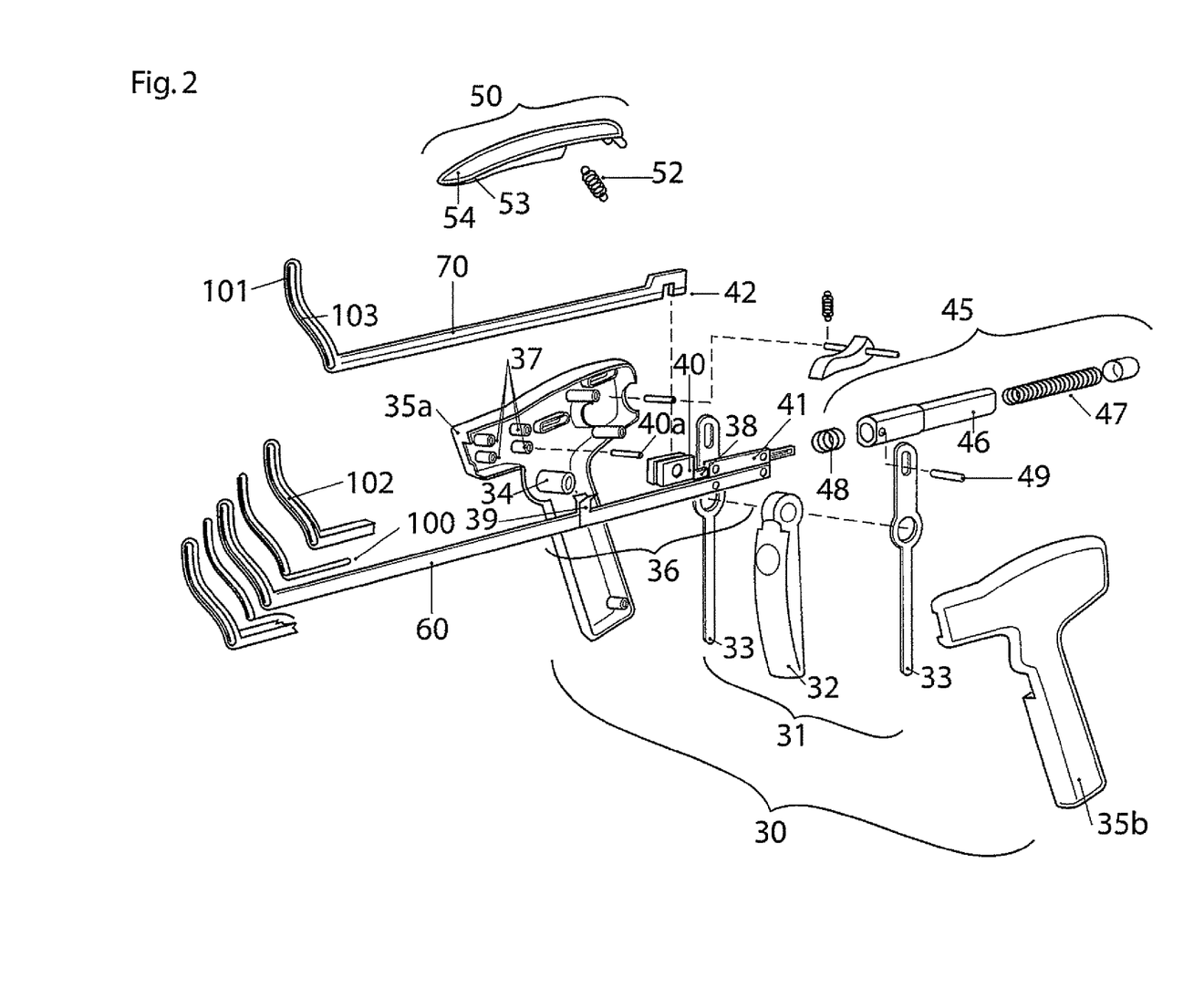
FIG. 2 is an exploded view of the two piece jaw bipolar ablation device of FIG. 1.

FIG. 2 is an exploded view of the electrosurgical device 25 showing the elements thereof. Closure trigger assembly 31 comprises trigger 32, and stiffeners 33 that assemble together and pivot on pivot boss 34 in a right cover 35a. First jaw 60 fixedly mounts in a lower jaw assembly 36. Lower jaw assembly 36 fits on and is retained between jaw bosses 37 within in a right cover 35a and within a left cover 35b.

Lower jaw assembly 36 includes first jaw 60 fixedly attached to a frame 38 having spreadable guide clamps 39 at a distal end. Spreadable guide clamps 39 spread apart and receive movable second jaw assembly 70 therebetween, and spring back when second jaw assembly 70 is fully seated. Spreadable guide clamps 39 both guide and releasably lock slidable second jaw assembly 70 to first jaw assembly 60. A second jaw fork assembly 40 slidably mounts within a proximal sleeve 41 of frame 38 and is electrically insulated therefrom. Second jaw fork assembly 40 operably connects to generator 26 via cable 27 (not shown). Second jaw fork assembly 40 has a pin 40a designed to be received in notch 42 at a proximal end of second jaw assembly 70 such that when second jaw assembly 70 is attached to handle assembly 30, longitudinal movement of second jaw fork assembly 40 results in longitudinal movement of second jaw assembly 70. Pin 40a also forms an electrical connection to second pole electrode 101 in second pole jaw assembly.

A clamp pressure assembly 45 has a housing 46, a proximal spring 47, a distal spring 48 and an actuation pin 49. Clamp pressure assembly 45 operably connects to the closure trigger assembly 31 and to the second jaw fork assembly 40 such that closure of the trigger assembly 31 moves second jaw fork assembly 40 and second jaw assembly 70 distally. Clamp pressure assembly 45 is provided to maintain a constant clamp pressure on different tissue thicknesses when the jaws of the first jaw assembly 60 and second jaw assembly 70 are closed together. Actuation pin 49 operably connects stiffeners 33 of trigger assembly 31 to housing 46, and to the longitudinally second jaw fork assembly 40 such that distal and proximal movement of closure trigger assembly 31 results in distal and proximal movement of second jaw fork assembly 40 and attached second jaw assembly 70. Springs 47, 48 are provided to maintain constant jaw clamp pressure independently of tissue thickness.

A releasable locking assembly 50 has a lever 51 and a spring 52 to close lever 51. Releasable locking assembly 50 is used to slidably lock or constrain the second jaw assembly 70 within the handle assembly 30. A laterally moving lock 53 is slidably located in lever 51 and has a hooked locking tab 54 extending therefrom. When releasable locking assembly 50 is closed to slidably capture the second jaw assembly 70, the lock 53 can be moved laterally towards left cover 35b to have hooked locking tab 54 lockingly engage with a wall of the left cover 35b. FIG. 1 shows the releasable locking assembly 50 in the clamped position with the locking lever 53 locked. A detent is provided to lock the locking lever 53 in the locked position. Unlocking locking lever 53 enables locking assembly 50 to be moved to the position of FIG. 4 and allows the removal of the second jaw assembly 70 from the surgical device 25.

Method of Use:

FIG. 3 shows a cross sectional view of a patient's chest and the first step in the method of use of the electrosurgical device 25. A small incision 110 has been placed into a patient's chest between a pair of ribs 111. In this view, the patient is upside down and a heart 112 is seen below a liver 113. The surgeon is inserting an angled first portion 104 of the first shaft assembly 60 into the incision 110 and into a thoracic cavity 114 of the patient.

Figure 4:
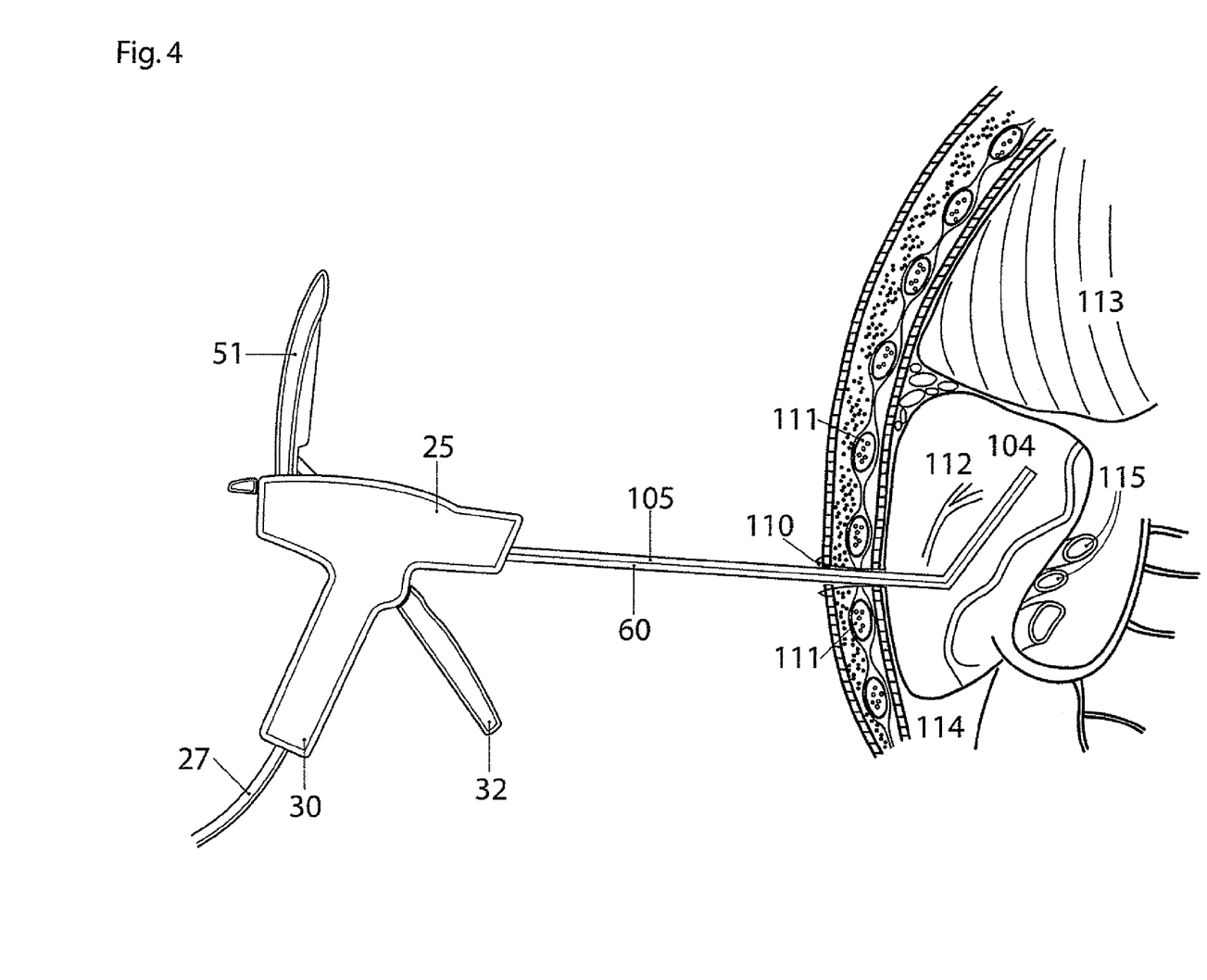
FIG. 4 is the partial cross sectional view of a patient's chest and heart of FIG. 3 with the first jaw assembly of the two piece jaw bipolar ablation device being rotated and inserted deeper near the heart and a jaw lock lever in an open position.

FIG. 4 shows the first shaft assembly 60 electrosurgical device 25 rotated to a new position in the thoracic cavity 114 of the patient with a straight portion 105 of the first shaft assembly 60 within incision 110. The handle assembly 30 can be seen. The surgeon has moved locking assembly 50 into the open position for the reception of the second jaw assembly 70 into the handle assembly 30.

Figure 5:
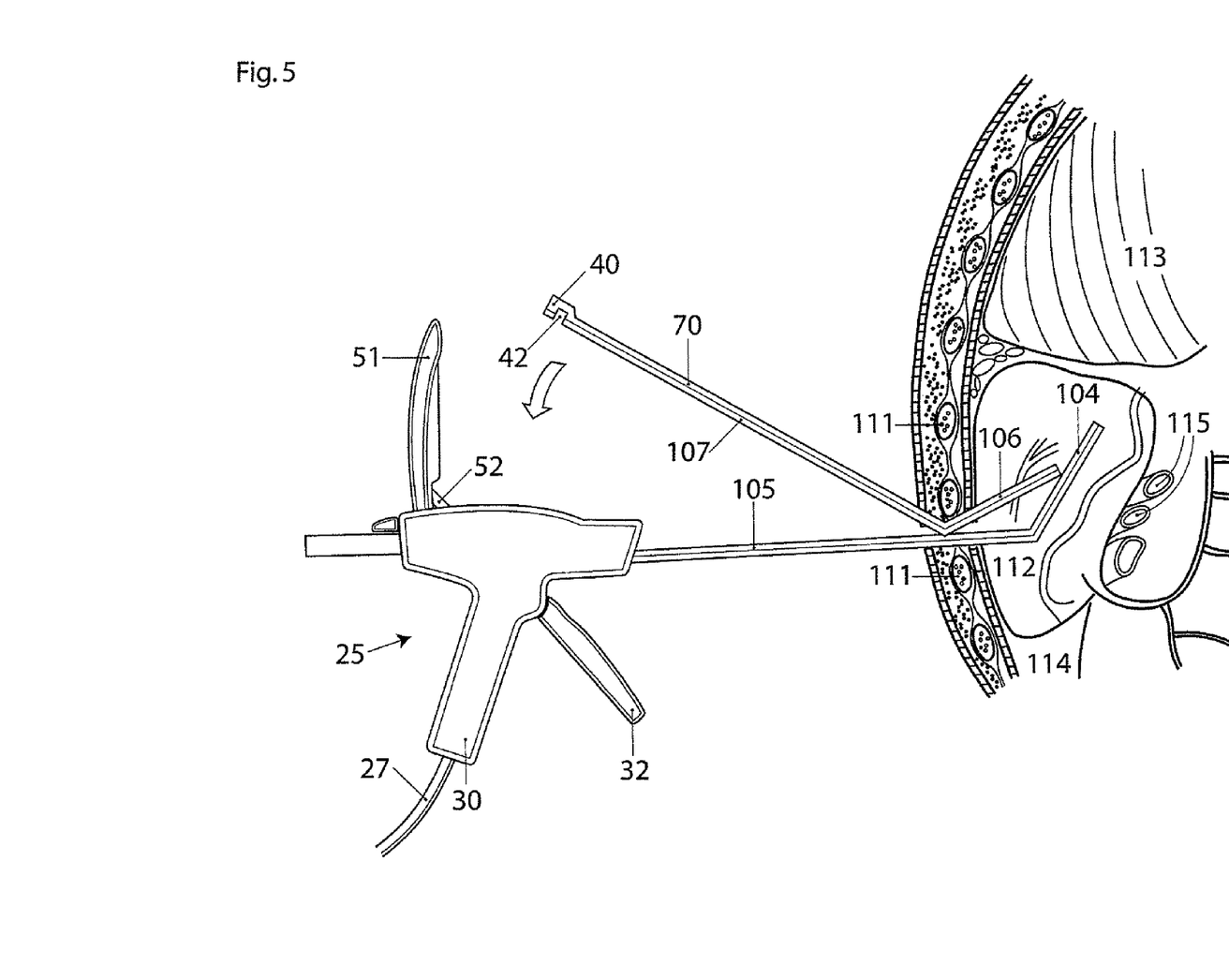
FIG. 5 is the partial cross sectional view of a patient's chest and heart of FIG. 4 with a second jaw being inserted between the ribs and rotated downward adjacent to the first jaw of the two piece jaw bipolar ablation device.

FIG. 5 shows the second jaw assembly 70 inserted into incision 110 and into the chest cavity 114. An angled second portion 106 of second jaw assembly 70 was first inserted into incision 110 with the electrode 101 parallel to a first long portion 105 of first shaft assembly 60. Angled second portion 106 was fully inserted into incision 110 and rotated into position as shown. As second jaw assembly 70 rotates into the position shown, a pair of wings 72 (best seen in FIGS. 8 and 11, and described below) extending downward between the angled second portion 106 and a second long portion 107 of second jaw assembly 70 swing around to engage with and straddle first jaw assembly 60. Wings 72 align second jaw 70 relative to first jaw 60 during the rotation process. A curved arrow is provided near slot 42 to show the direction of rotation.

Figure 6:
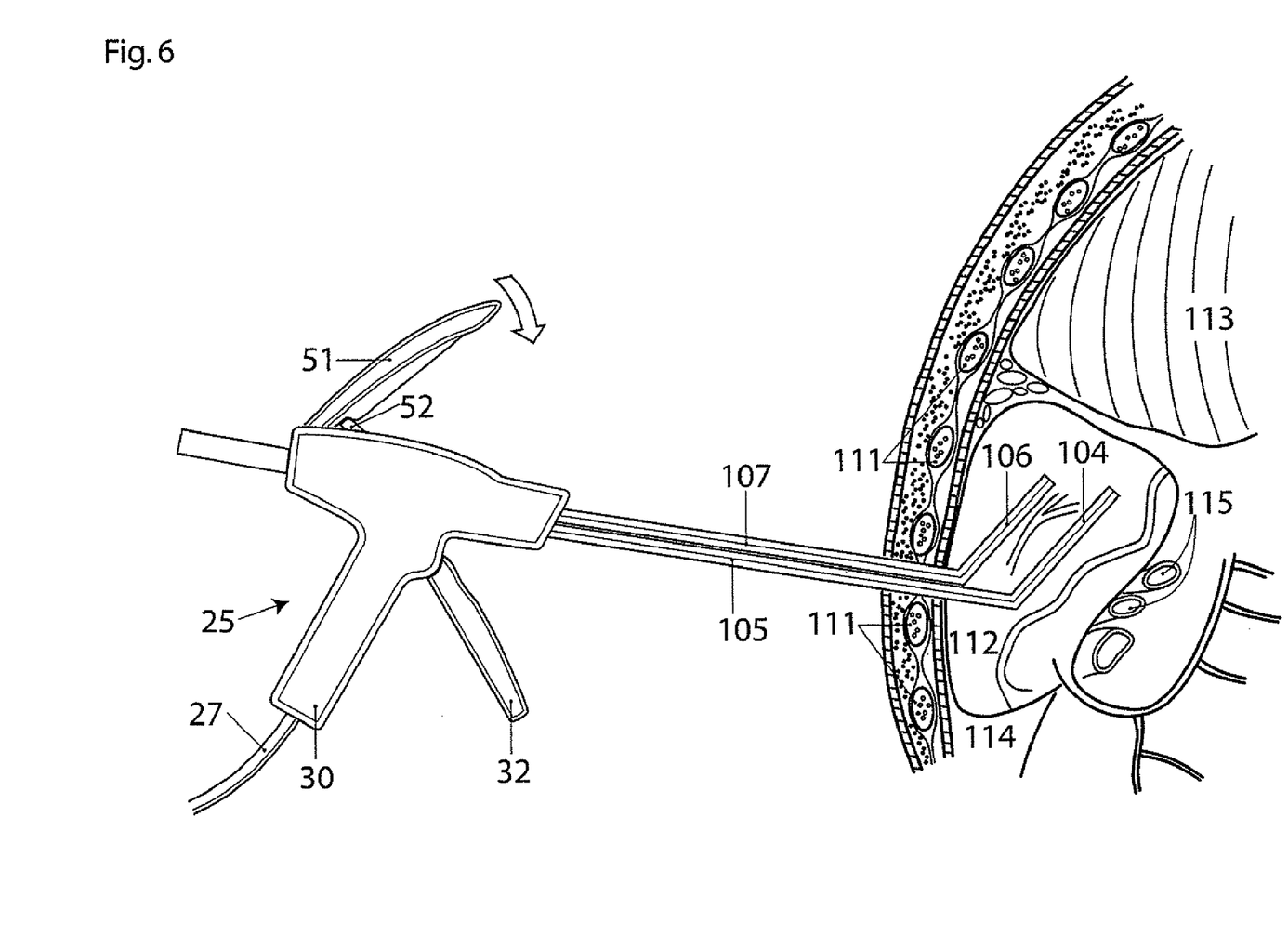
FIG. 6 is the partial cross sectional view of a patient's chest and heart of FIG. 5 with the second jaw assembly rotated downward into the two piece jaw bipolar ablation device with the jaw lock lever being rotated closed to secure the second jaw.

FIG. 6 shows the second jaw assembly 70 rotated into sliding engagement and alignment with the lower jaw assembly 60. Upper jaw assembly 70 is stabilized by wings 72 at a distal end that straddle lower jaw assembly 60, by spreadable guide clamps 39 in the center, and by handle assembly 30 at a distal end. Slot 42 of upper jaw assembly 70 is engaged with pin 40a in handle assembly 30 and second electrode 101 is electrically engaged with generator 27. The locking assembly 50 is shown rotating downwardly (see arrow) to slidingly secure the proximal end of upper jaw assembly 70 in handle 30.

Figure 7:
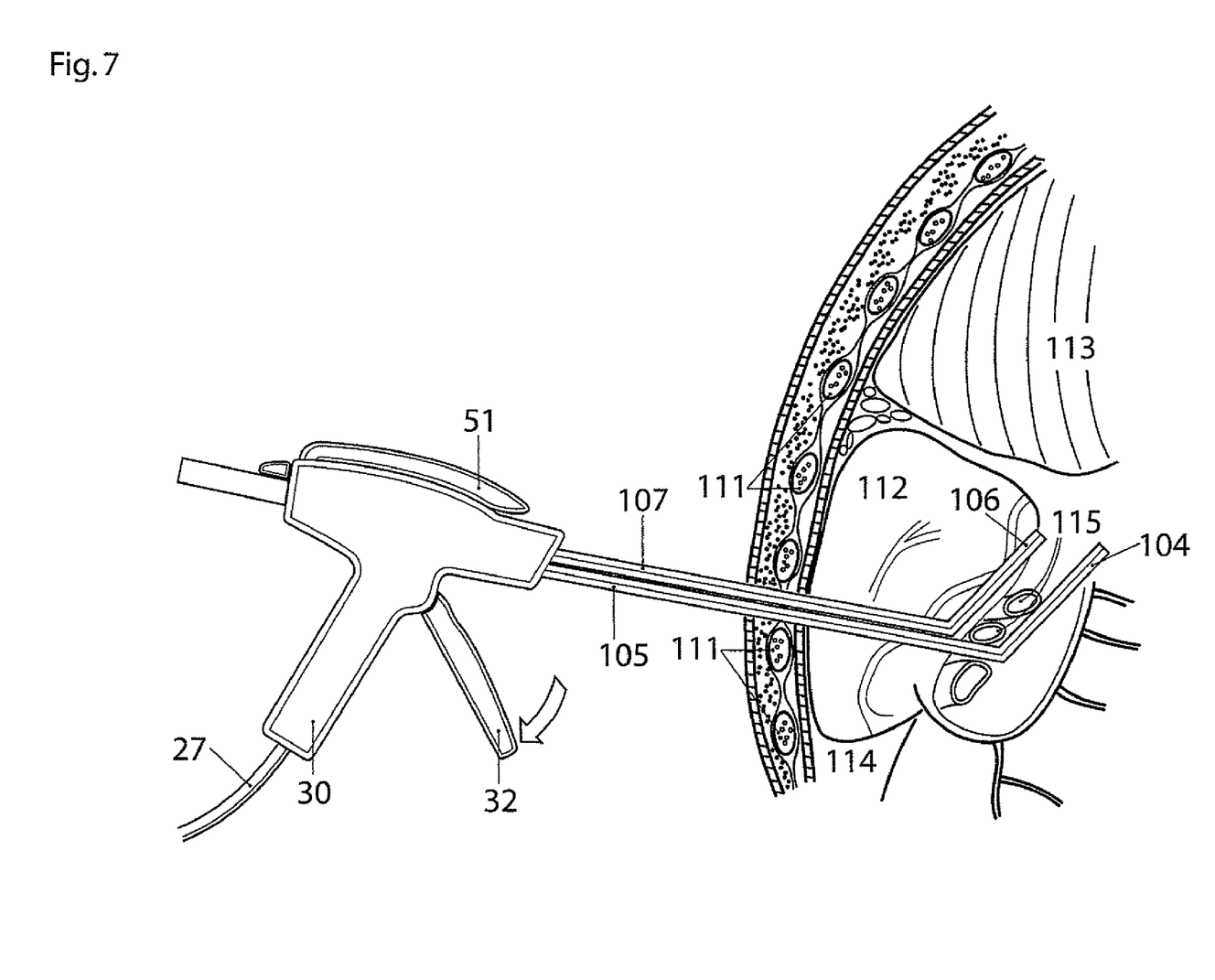
FIG. 7 is the partial cross sectional view of a patient's chest and heart of FIG. 6 with the second jaw of the two piece jaw bipolar ablation device with the jaw lock lever closed and a firing trigger being actuated to close the jaws on a pair of vessels.

FIG. 7 shows the surgical device 25 maneuvered into position around a pair of vessels 115. The locking assembly 50 is locked into position against covers 35a, 35b to secure the second jaw assembly 70 into the handle assembly 30. Trigger assembly 31 is partially actuated to move second jaw assembly 70 to the position shown about vessels 115. Further actuation of trigger assembly 31 will fully close the second jaw assembly 70 clamping vessels 115 between first jaw assembly 60 and second jaw assembly 70. When the jaws are fully closed, the generator 27 can be actuated to apply RF energy to the vessels 115 clamped between electrodes 100, 101.

Once all tissue is cauterized and/or coagulated with RF energy, the electrosurgical device 25 can be removed from the patient in an assembled or a disassembled configuration.

Jaw Alignment Mechanisms

Jaw alignment mechanisms are provided to slidingly align second jaw assembly 70 to the first jaw assembly 60. This alignment ensures the electrodes first pole electrodes 100, 101 are placed into alignment for proper coagulation when the second jaw assembly 70 is assembled to the first jaw assembly 60. The jaw alignment mechanisms can also help guide and align the first jaw assembly 70 with the first jaw assembly 60 during assembly.

Figure 8:
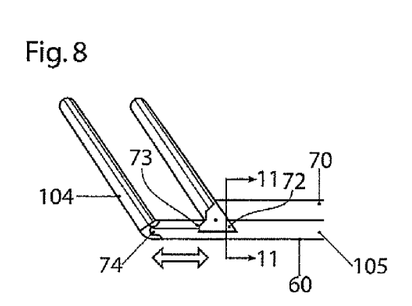
FIG. 8 shows a partial side view of the assembled first jaw and second jaw showing a first jaw interconnect and guidance mechanism.
Figure 11:
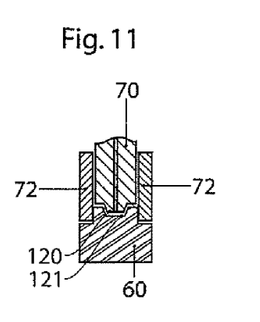
FIG. 11 shows a cross sectional end view of a shaft of the assembled first and second jaws of FIG. 9 showing a first set of guidance slots and ribs.

In FIGS. 8 and 11, the second jaw 70 is shown aligned onto the first jaw 60 by one or more wings 72 that extend from second jaw assembly 70 to straddle the first long portion 105 of first jaw assembly 60 and to provide side to side lateral alignment. As shown in FIG. 8 each of wings 72 can have an engagement member 73 extending distally that can be received in a socket 74 about the juncture of angled first portion 104 and first long portion 105. Wings 72 can have clearance with lower jaw assembly 60 and can provide longitudinal and vertical alignment by engaging engagement member 73 in a socket 74. Engagement member 73 and socket 74 can have matching angles or curves thereon to align the first pole electrode 100 with the second pole electrode 101. The alignment can be along the longitudinal axis and vertical axis during engagement.

Figure 12:
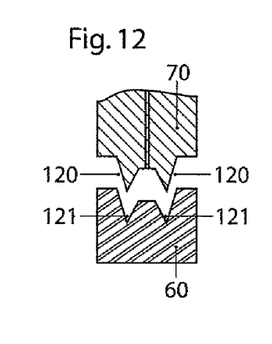
FIG. 12 shows a cross sectional end view of a shaft of the assembled first and second jaws showing a second set of guidance slots and ribs.
Figure 13:
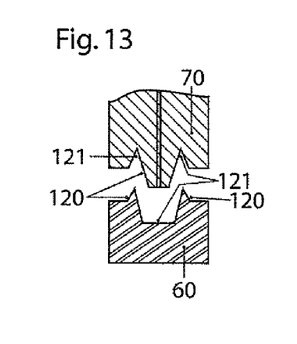
FIG. 13 shows a cross sectional end view of a shaft of the assembled first and second jaws showing a third set of guidance slots and ribs.
Figure 14:
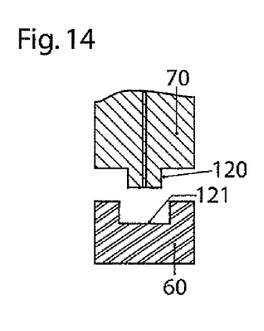
FIG. 14 shows a cross sectional end view of a shaft of the assembled first and second jaws showing a fourth set of guidance slots and ribs.
Figure 15:
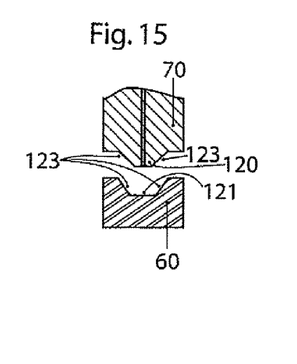
FIG. 15 shows a cross sectional end view of a shaft of the assembled first and second jaws showing a fifth set of guidance slots and ribs.

Alternately, as shown in FIGS. 11-15, one or more tongues 120 can extend downwardly from upper jaw assembly 70 and slidingly engage in one or more respective grooves 121 within lower jaw assembly 60 to provide alignment. As shown in FIGS. 11 and 14, tongue 120 has two parallel sides that align with and mount in mating sides in groove 121. In FIGS. 12, 13, and 15 each of the one or more tongues 120 have one or more angled side that mates with a mating angled side in groove 121. If desired, as shown in FIG. 11, the tongue 120 and groove 121 could be used in combination with wings 72. And, if desired, for example, the tongue 120 and groove 121 embodiments of FIGS. 11-15 could be flipped or reversed between the first jaw assembly 60 and the second jaw assembly 70 such that the groove 121 is in second jaw assembly 70 and the tongue 120 is in the first jaw assembly 60. Angled surfaces, 123 for example in FIG. 15 could be provided on the tongue 120 and groove 121.

Figure 9:
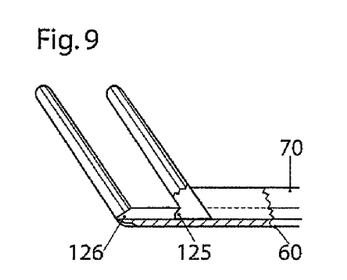
FIG. 9 shows a partial side view of the assembled first jaw and second jaw showing a second jaw interconnect and guidance mechanism with overlaps.

FIG. 9 shows an alternate example of another jaw alignment mechanism that can align second jaw assembly 70 to first jaw assembly 60 and first pole electrode 100 to second pole electrode 101. In this alternate example, the tongue 120 on second jaw assembly 70 has an angled prow 125 extending distally therefrom and the angled extension mates into an angled socket 126 within in groove 121. Any tongue and groove configurations such as shown in FIGS. 11-15 can be used for this embodiment and the tongue 120 and groove 121 can be reversed between jaw assemblies 60, 70.

Figure 10:
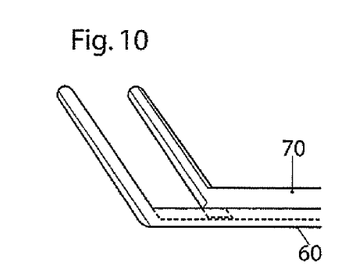
FIG. 10 shows a partial side view of the assembled first jaw assembly and second jaw assembly showing another jaw interconnect and guidance mechanism.

FIG. 10 shows another alternate embodiment of a jaw alignment mechanism having a plain tongue 120 in groove 121 alignment mechanism without an alternate alignment mechanism such as engagement member 73 and socket 74, and/or angled prow 125 and angled socket 126.

In addition, the alignment structure may also be interlocking in order to keep the jaws from separating after they are reassembled. To this end, the tongue and groove described above may be configured, in cross section, as a male and female dovetail, a T-shaped tongue and a T-shaped groove, or any other similar shapes where the tongue has a wide end coupled to the jaw by a narrow portion and the groove has a narrow entry that opens into a wider portion. Preferably, the cross-section of the slot transitions form a simple rectangular slot that clears the maximum width of the tongue at the proximal end of the jaw to a cross-section that more closely corresponds to the cross-section of the tongue so that the interlocking structures can be engaged during reassembly even if the jaws are not in parallel alignment, as seen in, e.g., FIG. 5.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present application describes several embodiments and while the illustrative embodiments have been described in considerable detail, it is not the intention of the applicant to restrict or in any way limit the scope of the appended claims to such detail. Additional advantages and modifications may readily appear to those skilled in the art.

What is claimed is:

1. An electrosurgical device for clamping and coagulating tissue between a pair of jaw assemblies, the jaw assemblies disassembleable outside of a patient and reassembleable within a patient, the electrosurgical device comprising:
   a handle assembly having a jaw actuator;
   a first jaw assembly extending longitudinally from the handle and having a first pole electrode at a first angle to the longitudinal axis; and
   a second jaw assembly having a second pole electrode and operably disassemblable and reassembleable with the first jaw assembly and the handle assembly, wherein when the second jaw assembly is operably assembled with the first jaw assembly and the handle assembly, the second pole electrode is about parallel to the first pole electrode and the second jaw assembly is operably coupled to the handle assembly such that actuation of the jaw actuator moves the second pole electrode to a clamped position with the first pole electrode and deactuation of the jaw actuator moves the second pole electrode to an unclamped position with the first pole electrode.

2. The electrosurgical device of claim 1 further including a first pole electrode wire operably coupled to the first pole electrode, and a second pole electrode wire operatively attached to the handle, the first pole wire and the second pole wire electrically conducting electrosurgical energy to the electrosurgical device.

3. The electrosurgical device of claim 2 further including an electrical connector attached to the second pole wire and operatively mounted within the handle assembly, wherein when the second jaw assembly is operatively assembled with the first jaw assembly and the handle assembly, the electrical connector electrically connects the second pole electrode to the second pole wire.

4. The electrosurgical device of claim 3 further including an alignment system between the second jaw assembly and the first jaw assembly, the alignment system slidably aligning the movable second jaw assembly with the fixed first jaw assembly.

5. The electrosurgical device of claim 4 wherein the alignment system includes one or more of a tongue in a groove, the tongue along one or more of the first jaw assembly and the second jaw assembly, and the mating groove along the other of the first jaw assembly and the second jaw assembly.

6. The electrosurgical device of claim 5 wherein each tongue has a pair of parallel tongue side walls and the groove has a pair of mating parallel groove side walls positioned for the sliding reception and alignment of the tongue therein.

7. The electrosurgical device of claim 6 wherein an angled closure alignment feature is on a distal extension of the tongue, and a mating angled receptacle is in a distal end of the groove, wherein when the second jaw assembly is closed, the angled closure alignment feature engages with the mating angled receptacle.

8. The electrosurgical device of claim 4 wherein each tongue has at least one angled side wall and the groove has a mating angled groove side wall for the sliding reception and alignment of the tongue therewith.

9. The electrosurgical device of claim 8 wherein the alignment feature is a pair of wings attached to the second jaw assembly about a proximal end of the second pole electrode, the wings straddling a longitudinal portion of the first jaw assembly and aligning the second jaw assembly to the first jaw assembly.

10. The electrosurgical device of claim 9 wherein the pair of wings includes at least one angled cam surface thereon and a mating alignment receptacle for each of the at least one angled cam surface on the other of the first jaw assembly and the second jaw assembly, wherein when the second jaw assembly is moved to a clamped position with the first jaw assembly, the least one angled cam surface is cooperatively constrained with the mating alignment receptacle.

11. The electrosurgical device of claim 1 further including a clamp pressure assembly within the handle assembly and operably coupled to a closure trigger, wherein when the second jaw assembly is operatively assembled to the first jaw assembly and the closure trigger is actuated, the clamp pressure assembly maintains a generally constant clamping pressure on tissue clamped between the first pole electrode and the second pole electrode.

12. The electrosurgical device of claim 1 wherein the first angle between the first pole electrode and the longitudinal axis of the first jaw assembly is about 30 degrees.

13. A method of using an electrosurgical device to clamp and coagulate internal tissue through a small incision within a patient, the method comprising the steps of:
   a) placing a first pole electrode of a first pole electrode assembly into the patient through the small incision;
   b) placing a second pole electrode of a second pole electrode assembly into the patient through the small incision wherein the second pole electrode assembly is separate and detached from the first pole electrode assembly;
   c) assembling the second pole electrode assembly to the first pole electrode assembly through the small incision within the patient to create an operative electrosurgical device;
   d) clamping internal tissue within the body between the first pole electrode and the second pole electrode
   e) coagulating internal tissue between the first pole electrode and the second pole electrode with an application of electrosurgical energy.

14. The method of claim 13 wherein the first pole electrode is at a first angle to the first pole electrode assembly and the step of placing the first pole electrode into the patient includes minimizing the area of the first pole electrode in the incision as the first pole electrode is inserted.

15. The method of claim 13 wherein the step of placing the first pole electrode into the patient further includes rotating the first pole electrode assembly about the first angle when the first angle is in the small incision to minimize the area of the electrode assembly during further insertion into the incision.

16. The method of claim 15 wherein the step of assembling the second pole electrode assembly to the first pole electrode assembly includes engaging aligning features between the first jaw assembly and the second jaw assembly in sliding engagement.

17. The method of claim 15 wherein the second pole electrode is at a second angle to the second electrode assembly and the step of placing the second pole electrode assembly into the patient includes placing the second pole electrode into the incision about parallel to the electrosurgical device to minimize the area of the electrosurgical device inserted in the small incision.

18. The method of claim 17 wherein the step of placing the second pole electrode into the patient further includes rotating the second pole electrode about the second angle when the second angle is in the incision, the rotation bringing the second pole electrode assembly into about parallel alignment with the first pole electrode assembly and minimizing the area of the electrosurgical device.

19. The method of claim 18 wherein the first pole electrode is connected to a source of electrosurgical energy and the step of assembling the second pole electrode assembly to the first pole electrode assembly includes connecting the second pole electrode to the source of electrosurgical energy.

20. The method of claim 17 wherein the step of assembling the second pole electrode assembly to the first pole electrode assembly includes constraining the second pole electrode assembly to the first pole electrode assembly in sliding engagement to prevent disassembly of the second jaw assembly from the first jaw assembly during operation.

* * * * *